United States Patent [19]
Sheridan

[11] Patent Number: 6,103,644
[45] Date of Patent: Aug. 15, 2000

[54] IMPREGNATED MATRIX AND METHOD FOR MAKING SAME

[75] Inventor: Christopher H. Sheridan, Cresskill, N.J.

[73] Assignee: Nordico Marketing Development, Inc., New York, N.Y.

[21] Appl. No.: 08/868,344

[22] Filed: Jun. 3, 1997

Related U.S. Application Data

[63] Continuation-in-part of application No. 08/560,035, Nov. 17, 1995, abandoned, which is a continuation-in-part of application No. 08/171,676, Dec. 22, 1993, abandoned.

[51] Int. Cl.[7] ...................................................... A61F 13/00
[52] U.S. Cl. .............................. 442/123; 442/84; 442/91; 442/121; 428/311.11
[58] Field of Search ................................ 442/84, 91, 97, 442/121, 123; 428/305.5, 311.11

[56] References Cited

U.S. PATENT DOCUMENTS

| | | | |
|---|---|---|---|
| 2,944,931 | 7/1960 | Yang | 162/179 |
| 3,912,666 | 10/1975 | Spitzer et al. | 260/2.5 E |
| 4,565,644 | 1/1986 | Smith et al. | 252/92 |
| 4,690,821 | 9/1987 | Smith et al. | 424/401 |
| 5,091,102 | 2/1992 | Sheridan | 252/91 |
| 5,334,388 | 8/1994 | Hoang et al. | 424/402 |
| 5,980,931 | 11/1999 | Fowler et al. | 424/443 |
| 5,997,887 | 12/1999 | Ha Kim et al. | 424/401 |

*Primary Examiner*—Daniel Zirker
*Attorney, Agent, or Firm*—Evelyn M. Sommer

[57] ABSTRACT

A substantially flexible, dry matrix, which contains not more than about 3% moisture at room temperature, is impregnated with a water free treatment mixture containing a lipid and a surfactant. In a preferred embodiment, the mixture includes a glycol, a surfactant and a lipid emollient, lubricant, medicament or skin protectant. Methods for manufacturing and using the impregnated matrices are also taught.

23 Claims, No Drawings

IMPREGNATED MATRIX AND METHOD FOR MAKING SAME

This application is a continuation-in-part of application Ser. No. 08/560,035, now abandoned, filed Nov. 17, 1995, which in turn is a continuation-in-part of application Ser. No. 08/171,676 filed Dec. 22, 1993 now abandoned.

BACKGROUND OF THE INVENTION

1. Field of the Invention

The present invention relates to a treated matrix and method for making and using the same. More particularly, the present invention relates to a matrix treated with at least one lipid, emollients, lubricants, antimicrobial agents, skin protectants or medicaments and a surfactant. This matrix transfers the lipid to a skin surface as a thin film on contact.

2. Description of the Art

Heretofore, emollients, protectants, medicaments and lubricants that are slightly, or not, soluble in water have been applied using emulsions of oil and water. Examples of such emulsions include skin lotions and other skin care products. However, such emulsions are non-uniform, separate, and are susceptible to bacterial growth. While the addition of surfactants improves and extends the life of emulsion, such additions do not solve the problems since oil and water simply do not mix. Moreover, such compositions are difficult to formulate and apply.

U.S. Pat. No. 5,091,102, entitled Method of Making a Dry Antimicrobial Fabric, issued to Sheridan, the applicant herein, on Feb. 25, 1992, and was assigned to the same assignee as the present application. This patent is directed to a method of making a substantially flexible dry matrix or towel for use in cleaning a surface by removing dust and/or organic film products. The Sheridan U.S. Pat. No. 5,091,102 matrix includes a glycol compound, a cationic surfactant, and antimicrobial agent and, in a preferred form, a nonionic surfactant, each of which is water soluble.

As disclosed in Sheridan U.S. Pat. No. 5,091,102, in example 1 thereof, at col. 9 line 40–col. 10 line 23, commercially available dust cloths cannot clean a surface because they are incompatible with water and leave an oil-in-water smear behind. Even when squeezed dry, they are oily and create more dirt to be cleaned. The invention described in Sheridan U.S. Pat. No. 5,091,102 solved the problem by being able to clean with water. Because the components are water soluble, they are able to clean the surface with water. Sheridan's success was attributable to restricting the cleaning components to water soluble materials.

Sheridan U.S. Pat. No. 5,091,102, however, did not address the specific problem confronted herein, namely providing a vehicle or matrix for transferring an emollient, lubricant, protectant, and/or medicament where at least one of the components was water insoluble as defined in the CRC Handbook of Chemistry and Physics, i.e., an emollient, petrolatum, zinc oxide, vitamin A, vitamin D, zinc carbonate, etc., or of low water solubility, i.e., slightly soluble[1] in water such as zinc citrate, zinc phenate, sulfadiazole, sulfa-guanidine, citronellol, hydantoin, etc. As used herein, the terms soluble and slightly soluble are used in the conventional sense (see Hackh's Chemical Dictionary, for example). This is particularly applicable to transferring a skin care product to the skin from the matrix.

[1] Slightly soluble—soluble in water on a relative scale: 1=insoluble, 2=slightly insoluble, 3=soluble, 4=very soluble, 5=miscible (CRC Handbook of Chemistry and Physics, 75th Edition, David R. Gide, page 1–3). Soluble— capable of mixing with a liquid (dissolving) to form a homogeneous solution. The degree of solubility may conventionally be expressed: very soluble—less than 1 part solvent freely soluble—from 1 to 10 parts solvent soluble—from 10 to 30 parts solvent sparingly soluble—from 30 to 100 parts solvent slightly soluble—from 100 to 1000 parts solvent very slightly soluble—from 1000 to 10,000 parts solvent insoluble—more than 10,000 parts solvent needed to dissolve 1 part substance (solute). (Hackh's Chemical Dictionary, 3d Edition, p.787.)

SUMMARY OF THE INVENTION

Against the foregoing background, it is a primary object of the present invention to provide a dry matrix which is impregnated with a mixture of at least one liquid surfactant and a lipid such as an emollient, a lubricant, a medicament and/or a skin protectant[2].

[2] "[L]ipids are material which are soluble in organic solvents and essentially insoluble in water." R. M. Burton & F. C. Guerra, FUNDAMENTALS OF LIPID CHEMISTRY, 2 (1974).

It is another object of the present invention to provide a method of making the impregnated matrix of the present invention.

It is a further object of the present invention to provide a substantially water-free treated matrix for shipping.

It is yet a further object of the present invention to provide a treated matrix that does not require packaging effective to prevent the evaporation of water or solvents.

It is yet another object of the present invention to provide a treated matrix that is microbially stable, even when not packaged within a moisture migration barrier.

It is a still further object of the present invention to provide such a matrix which, when exposed to water and pressure, will substantially instantaneously form an emulsion which can serve to transfer the surfactant, the emollient, lubricant, medicament and/or protectant from the matrix to a skin surface.

To accomplish these and other objects of the present invention, the composition of the present invention comprises a substantially flexible, dry matrix having a moisture content not exceeding about 3%, impregnated with a water-free treatment mixture. The matrix is adapted to transfer lipid components in said treatment mixture to a skin surface on contact. The treatment mixture preferably includes at least one liquid surfactant and at least one lipid. The lipid is preferably selected from the group of emollients, lubricants, medicaments and skin protectants. A method for forming said impregnated matrix is further provided as is a method for applying a lipid emollient, lubricant, medicament and/or protectant mixture to skin.

BRIEF DESCRIPTION OF THE PREFERRED EMBODIMENTS

The present invention relates to a substantially dry matrix or matrix of the type which is described, for example, in U.S. Pat. No. 5,091,102, the disclosure of which is hereby expressly incorporated herein by reference thereto. Such matrix is substantially dry and is devoid of any water other than the water which may be naturally present in the matrix as manufactured and the matrix remains dry to the touch after impregnation with the treatment mixture. A typical matrix for use in the present invention is a cellulosic material, which while dry to the touch, may contain up to about 3% water.

As used herein, the term matrix may further include the finished matrix, cloth or towel product, i.e., a wipe, garment, etc.

A useful matrix may contain natural or synthetic fibers, processed into woven, non-woven or knitted form, a flexible foam, or combinations thereof, in a basis weight range generally of between 5 and about 200 grams per square yard and preferably between 15 and about 100 grams per square yard. A preferred matrix is comprised of woven or nonwoven thermoplastic filaments or fibers, preferably of polypropylene, with a basis weight range of between about 5 and about 100 grams per square yard, preferably between 15 and 40 grams per square yard. The tensile strength of such a matrix must be sufficient to enable the wipe to be used without shredding or disintegrating and should generally be between about 0.5 and about 1.5 pounds per inch of width. The matrix can consist of a single layer of the filaments or fibers or a foam layer or it can consist of a plurality of layers of the same filaments or fibers and/or foam which have been adhered by using any suitable method such as sonic, thermal or mechanical bonding, etc. Final selection of the matrix will, of course, depend upon its actual intended application.

Particularly preferred matrices include fibers selected from the group consisting of polypropylene, polyester, nylon and cellulosics, such as cellulose, cotton, rayon, hemp, etc. and foams selected from the group consisting of polyurethane, polypropylene, polyethylene, polyester, etc.

A treatment mixture preferably consists of at least one surfactant and a lipid emollient, and/or protectant, and/or a medicament, and/or lubricant. The treatment mixture is applied to the matrix and impregnated therein. When the matrix is applied to skin, the lipid is readily transferred thereto and remains on the skin as a film. In another aspect of the present invention, when the matrix is exposed to water at the point of use and pressure is applied by squeezing, or rubbing, the matrix, the treatment mixture forms an unstable emulsion which maybe adapted to release the lipid onto the skin.

The treatment mixture preferably includes a glycol, and more preferably propylene glycol, USP, although any glycol which is safe, nontoxic and possesses the ability to coat fibers uniformly may be used. The glycol used desirably imparts a softness to the dry matrix. The glycol may act as a non-ionic liquid surfactant, or in any other conventional capacity for which glycol is used in the cosmetic and pharmaceutical industries.

Polyethylene glycol and CARBOWAX® (methoxy polyethylene glycol), may also be used in the present invention. These compounds are members of a family of linear polymers formed by the addition reaction of ethylene oxide. The generalized formula for polyethylene glycol is:

HO—(CH$_2$CH$_2$O)$_n$—H and for the methoxy polyethylene glycol is:

CH$_3$O—(CH$_2$CH$_2$O)$_n$—H wherein "n" is the average number of repeating oxyethylene groups. The repeating ether linkages and terminal hydroxyl groups give rise to the water solubility of the polyethylene glycol.

Polyethylene glycol is generally available in average molecular weights ranging from 200 to 8000 and methoxy polyethylene glycol is available is average molecular weights ranging from 300 to 5000.

The treatment mixture typically contains a glycol in an amount between 1% and about 99% by weight of the treatment mixture and, preferably, between about 4% and about 50% by weight.

The treatment mixture optionally also contains other nonionic and cationic surfactants, either separately or in combination. The cationic and nonionic surfactants described in U.S. Pat. No. 5,091,102, the disclosure of which is hereby incorporated herein by reference, may be used in the present invention. Preferred cationic surfactants can be selected from any of the well-known classes of water soluble quaternary ammonium compounds. Such classes include the quaternary heteronium[3] compounds such as cetyl pyridinum chloride and polymeric quaternary compounds of the general formula:

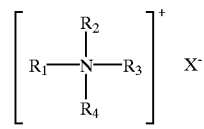

wherein $R_1$ and $R_2$ are selected from an alkyl group, an alkyl ether group and a hydroxyalkyl group each containing from 1 to 3 carbon atoms, $R_3$ is an alkyl group containing from 6 to 20 carbon atoms, and $R_4$ is selected from an alkyl group containing 6 to 20 carbon atoms, an aralkyl group wherein alkyl contains 1 to 2 carbon atoms and heterocyclic radicals and X$^-$ is a suitable anion such as halide, e.g., chloride, bromide and iodide or nitrate, methosulfate or acetate.

[3] The term "heteronium compound" is defined in Hackh's Chemical Dictionary, 4th Edition, as a "hetero—prefix (Greek) indicating unlikeness or difference" and "onium—suffix and indicating a complex cation . . . "

A particularly useful compound having the general formula listed above is one wherein R and $R_1$ and $R_2$ are alkyl groups having 1-3 carbon atoms, $R_3$ is an alkyl benzyl group such as dodecylbenzyl, $R_4$ is a polypropylene oxide group, and X is chloride.

Particularly useful quaternary ammonium compounds of the above-indicated general formula are the $C_{8-18}$ alkyl dimethyl ammonium chlorides and mixtures thereof.

Examples of such cationic surfactants which may be used include: Stepan BTC 2125M or BTC 65.

The preferred amount of cationic surfactants compound to be included in the treatment mixture in accordance with the present invention ranges between about 0.5% and about 50% by weight, and preferably is between about 1% and about 25% by weight.

The preferred glycol compounds themselves exhibit nonionic surfactant properties. In addition, however, depending upon the specific end use to which the matrix is to be put, the mixture may also be optionally contain up to about 0.5% to 50% by weight of another nonionic surfactant in addition to the glycol specified herein. Suitable nonionic surfactants include those selected from the group consisting of:

(a) the polyethylene oxide condensates of alkyl and dialkyl phenols, having a straight or branched alkyl group of from about 6 to about 12 carbon atoms with ethylene oxide, wherein the amount of ethylene oxide present is from about 3 to about 25 moles per mole of alkyl phenol;

(b) the condensation products of aliphatic alcohols with ethylene oxide of the formula RO (C$_2$H4O)$_n$H and/or propylene oxide of the formula RO (C$_3$H$_6$O)$_n$H: wherein in either or both cases R is a straight or branched alkyl group having from about 8 to 22 carbon atoms, and n is 3 to 40;

(c) polyoxyethylene polyoxypropyl block polymers.

When employed in accordance with the present invention, the nonionic surfactant may be present in the treatment mixture in an amount up to about 50% by weight of the treatment mixture and, preferably, in an amount between 0.5 to 50% and most preferably about 5% and about 40% by weight of the total mixture.

The surfactant composition used in the dry matrix of the present invention may alternatively comprise a non-ionic and an anionic surfactant.

It is also desired that the surfactant composition used in the dry matrix of the present invention has a hydrophilic-lipophilic balance between about 4 and 11.

As previously stated, the treatment mixture further contains a lipid which can be one or more members of the group of emollients, lubricants, surface protectants, and medicaments for transfer to the skin surface.

Useful emollients include stearyl ethers and caproic esters. Emollients serve to soften skin. A particularly preferred emollient is a caprylic/caproic ester, most preferably the product sold by HULS America under the trademark MYGLIOL 812[4].

[4] insoluble in water.

The emollient should be included in the treatment mixture in an amount between about 5% and about 70% by weight of the treatment mixture and, preferably, in an amount between about 20% and about 40%.

Useful lubricants include mineral oil[5] petrolatum[6] and wax[7]. Lubricants serve to protect skin and prevent moisture loss. They also function as humectants. A particularly preferred lubricant is mineral oil and, most preferably, the mineral oil product sold by J. T. Baker under the trademark Mineral Oil USP. The lubricant may be included in the treatment mixture in an amount between about 1% and about 50% by weight of the treatment mixture and, preferably, in an amount between about 1% and about 15%.

[5] Insoluble in water.
[6] Insoluble in water.
[7] Insoluble in water.

Useful protectants include the polysiloxanes[8], dimethicone[9] and cyclomethicone[10]. A particularly preferred protectant is dimethyl polysiloxane, and most preferably, the silicone product sold by General Electric, under the trademark Silicone Fluid SF96-350.

[8] Insoluble in water.
[9] Immiscible in water.
[10] Immiscible in water.

The protectant, when so included, should comprise between about 5% and about 50% by weight of the treatment mixture and, preferably, be present in an amount between about 10% and about 25%. It will be appreciated, however, that the actual amount of protectant will vary depending upon the particular protectant and the application.

In a similar manner, medicaments such as, for example, zinc oxide[11], aloe, titanium dioxide[12], sulfadiazine[13], sulfaguanidine[14], citronellol[15] and the like can also be included for application to the skin surface. Other pharmacological agents that could be included would be (a) vitamins A, C, D, E[16] etc. (b) antimicrobials such as bacitracin, neomycin, miconazole, oxyquinoline, polymycin, and the like, (c) anti-inflammatory agents such as steroids, (d) antihistamine agents such as benadryl, (e) anti-acne agents such as salicylic acid or retinoic acid[17] etc.

[11] Insoluble in water.
[12] Insoluble in water.
[13] Sparingly soluble in water.
[14] Sparingly soluble in water.
[15] Very slightly soluble in water.
[16] Insoluble in water.
[17] Insoluble in water.

It will of course be appreciated that the treatment mixture may contain the lipid emollients, lubricants, protectants, and medicaments, either singularly or in combination, depending upon the particular application.

In order to prepare an impregnated matrix, a treatment preparation is made by strongly agitating the components. This preparation is added to the matrix.

The matrix may be prepared in the manner described in U.S. Pat. No. 5,091,102. Commercially manufactured matrices may also be used such as, for example, DuPont's Sontara matrix which consists of a mixture of cellulosic and synthetic fibers normally supplied in a basis weight of 62 grams per square yard.

The matrix is then coated with the treatment mixture using a conventional transfer process such as, for example, the process described U.S. Pat. No. 5,091,102. In such process, continuous rolls of the matrix are passed between an engraved roller and a smooth roller under pressure. The engraved roller includes a plurality of cells and cavities that are defined by specific shape and dimensions. During operation, the engraved roller is partially submerged in the treatment mixture and rotates there through causing the mixture to fill the cavities of the engraved portions of the engraved roller. Excess mixture which may accumulate is removed by a doctor blade. The mixture remaining in the cells of the engraved roller is transferred by way of pressure absorption and surface tension into the matrix as it passes under pressure between the engraved roller and smooth roller. It will, of course, be appreciated that the treatment mixture may also be applied to the matrix by other treatment methods such as spraying, dipping, extrusion or reverse rolls.

The treated matrix containing the predetermined measured volume of treatment mixture may be wound onto rolls and/or is converted into the desired product.

The "water-free" treated matrix is dry to touch on fabrication, no separate drying step being required to dry the same.

The impregnated or treated matrix may then be used for direct application of the emollient, lubricant, medicament and/or surface protectant to the skin. When such matrix is placed in contact with the skin, the lipid is transferred out of the matrix and onto the skin in the form of a thin film. Furthermore, when the treated matrix is exposed to water at the point of use and sufficiently squeezed, or rubbed, the glycol, surfactants and emollient, protectant, medicament and/or lubricant substantially instantaneously form an emulsion with the water, which can transfer the lipid to the skin surface.

It will be appreciated that the treated or impregnated matrix containing non-aqueous components can be composed of one layer or multiple layers.

When the matrix or wipe of the present invention is first treated with the mixture of partially water and oil soluble surfactants and emollients, antimicrobial agents, lubricants and/or medicaments, at least one of which is a lipid, the lipid material is believed to be absorbed on the lipophilic portion of the fibers composing the matrix and spreads to form a thin film. When the treated wipe is contacted with water at the point of use, the aqueous phase is also absorbed by the hydrophilic portion of the fibers and spreads to form a thin film. However, the emulsion does not form (to any substantial degree) until (shear) energy (rubbing) is applied to mix the matrix surfaces. The two immiscible phases are both present absorbed on the surfaces of the fibers as high surface area films in close contact. Rubbing the matrix or treated wipe on skin, creates sufficient shear energy to overcome the viscous resistance of the liquids and disperses the oil phase in the aqueous phase creating an instant emulsion. The emulsion transports the lipid material to the skin surface. Once the shearing action stops, the emulsion breaks and the phases once again separate on the matrix fiber. The emulsion reforms when energy, i.e. rubbing, resumes. It should be noted that without the emulsion, the lipid remains on the matrix.

In an alternative application of the treated matrix of the present invention, the matrix is moistened and rubbed just before use to form an unstable emulsion that is effective to transfer a lipid to a skin surface when the skin is wet.

An emulsion is a dispersion of a first liquid in a second immiscible liquid. Since most emulsions contain water as one of the two phases, emulsions are usually classified as either an oil-in-water (O/W) emulsion having droplets of oil dispersed in a continuous water phase, or a water-in-oil (W/O) emulsion having droplets of water dispersed in a continuous oil phase. The continuous liquid, or phase, is referred to as the dispersion medium, and the discontinuous liquid, or phase, is the disperse phase.

One cannot prepare a stable emulsion of two pure immiscible liquids. Rather, an emulsion requires a third component: an emulsifying agent or surfactant. Generally, adding a surfactant lowers the interfacial tension of the two phases which allows an emulsion to form when the two immiscible liquids are mechanically agitated. During agitation, both liquids form droplets with one of the liquids becoming continuous and the other remaining in droplet form when an emulsifier (a stabilizing compound) is included in the agitated mixture. However, if this mixture of droplets does not include the emulsifier, the droplets will separate into two phases when the agitation ceases.

The type of emulsion, O/W or W/O, is determined in part by the volume ratio of the two liquids, provided the ratio is sufficiently high. For example with a 5% water and 95% oil volume present (an oil to water phase ratio of 19), the emulsion will be a W/O type. For moderate ratios (between about 0.3 and 3), the type of emulsion is determined by several such as the order of addition and the type of emulsifier. One liquid slowly added to the other with agitation usually results in the last added phase being the continuous one. Moreover, the phase in which the emulsifier is most soluble is generally the continuous phase. For example, water soluble soaps stabilize oil-in-water emulsions whereas water insoluble soaps stabilize water-in-oil emulsions.

Emulsification creates new surfaces between the two phases, namely the surfaces between the droplets. Such surface creating processes require energy: the surface free energy. Numerically, the surface free energy is identical to the surface tension. However, most of the energy consumed during emulsification is used to overcome the viscous resistance of the liquids during agitation, and not to enlarge the interface. As a consequence, low viscosity liquids are easier to emulsify than high viscosity fluids. Based on this observation, it is preferred that the viscosity at 25° C. of the lipid material used in the present invention is less than about 300 cps.

Through the use of agitation or shear forces, emulsification usually breaks the original phases into progressively smaller droplets. Variations in the mode of agitation, the nature and amount of emulsifying agent, pH and temperature changes also affect emulsification.

Commercial applications usually require emulsions to be stable for months, if not longer. But, how stability is defined, and how it is measured, depends upon the specific application. Nonetheless, when an emulsion breaks down, the dispersed droplets coalescence, or flocculate. During flocculation, droplets combine into large droplets until finally the droplets achieve an observable separate phase. A fully separated emulsion consists of separate oil and water layers.

Both the charge at the interface and the packing of the emulsifier molecules effect the stability of an emulsion. Emulsions with a small average droplet size are more stable. For this reason, commercial emulsions are often prepared with homogenizers that rapidly reduce droplet sizes.

While a low viscosity makes emulsification easier, a high viscosity retards flocculation, and thus improves the emulsion's stability.

The treated matrix of this invention is impregnated with a mixture of a liquid surfactant and a lipid, which preferredly is a skin protectant, antimicrobial agent and/or emollient.

In an alternative embodiment, directly before use, at least about three parts, by volume, of water is added to each part, by volume, of the treated matrix. The towel is then rubbed on skin. This rubbing provides sufficient shear and agitation to uniformly disperse the lipid phase in the water phase which facilitates the transfer of the active ingredients to the skin surface. To achieve this instant emulsion under low shear conditions of the type encountered when the skin is rubbed with a wipe, sufficient surfactant that is partial solubility in both phases must be present to reduce the interfacial tension and facilitate the substantially instantaneous formation of the emulsion. In addition, the viscosity of the dispersed and continuous phase are desirably kept low by using a lipid with a low viscosity. Such lipids readily emulsify upon application of "rubbing" shear. While this emulsion breaks when the matrix is quiescent (i.e., when the rubbing stops), it reforms with further rubbing.

To achieve the instant emulsion under low shear of this invention, the surfactants are desirably present in an amount of at least about 15% by weight of the lipids, and preferredly between about 15 and 50% by weight. These surfactants also should exhibit partial solubility in both the continuous phase (here, water) and dispersed phase (here, lipid) so that the interfacial tension is quickly reduced.

Unlike pre-prepared stable emulsions encountered in commercial products heretofore, the stability of this in situ formed emulsion once the rubbing (aggitation) stops is not importent. In a preferred embodiment of the present invention, the uniformly dispersed emulsion only exists while the matrix is being agitated, i.e., rubbed. Nonetheless, this short lived emulsion is effective to transfer the disperse phase from the matrix to the rubbed skin surface.

Ordinarily, the low shear created by rubbing a treated wipe on a skin surface is insufficient to emulsify two immiscible liquids, particularly when the two insoluble liquids are in a test tube or mixing tank. The success of this invention is based on the substantially instantaneous creation of the emulsion on the fibers of the treated matrix. There, the two liquid phases exist as thin films coating the matrix fiber surface, which results in a high surface area films. In the presence of surfactants, these high surface area thin films mix intimately and emulsify under low shear.

The invention will be illustrated by the following examples which are not to be construed in limitation thereof:

EXAMPLE I

Emollient

A matrix, composed of air laid cellulose and acrylic binders weighing approximately 60 grams per yard square was treated with a non aqueous mixture of lipid emollients and surfactants as set forth below.

The matrix is suitable for use as a moistened baby wipe. The treatment mixture described below was added to the matrix by using a gravure printing mechanism, the gravure pattern roll of which contains a uniform geometric cellular structure and turns within a reservoir of treatment mixture. Any excess mixture being removed by intimate contact with a doctor blade, transferring the treatment mixture from its cellular structure to said matrix as the matrix passes over the gravure roll while under pressure exerted upon the matrix by a smooth roll parallel to, and above, the gravure roll.

The treatment mixture was added to the matrix in an amount of 10% of the weight of the matrix. Rolls of water-free treated matrix, which are dry to the touch, were converted into 7"×8" "Z" folded, tab connected towels.

Stacks of these treated towels containing 80 folded tab-connected sheets, were placed in a dispensing container. Individual towels made from the water-free treated matrix were applied directly to the skin. This application left a thin film of the treatment mixture on the skin which softened the skin appreciably. These same towels, when contacted with wet skin, created an unstable emulsion, which allowed for both cleansing and softening of the skin.

In one trial, an amount of water equal to three times the weight of the towel stack was added at one time and the wetted towels dispensed through an opening provided in the container. The towels functioned as well as a standard Scott brand Baby Fresh Moist Towel as a cleaner. The unique difference however, is that in addition to cleaning skin, the towel of the present invention transferred the emollients to the skin. Panels of adults who used the towels of the present invention could discern the added emollience.

| CHEMICAL COMPONENT | TRADE NAME | AMOUNT |
| --- | --- | --- |
| Caprylic/Caproic Ester | Miglyol 812 | 30.00 |
| Poly Oxypropylene 15 Stearyl Ether | Arlamot-E | 41.00 |
| Polysorbate 85 | Tween | 18.10 |
| Propylene Glycol USP | | 4.80 |
| Benzalkonium Chloride | BTC-6 | 4.80 |
| Dowcil 200 | | 0.30 |
| Fragrance | | 1.00 |
| | | 100.00 |

EXAMPLE II

Lubricant

Example I shows that a lipid emollient can be placed uniformly on the skin by contact using a water free towel or a moistened towel with pressure to create an unstable emulsion. This example shows that a lipid lubricant can be applied in a similar manner.

A polyethylene and/or polypropylene fiber matrix having a basis weight of approximately 20 grams per square yard was treated with the following formula at the rate of 100% of basis weight yielding an add on of mineral oil (a lubricant) at 9–10%. At this level of treatment, the matrix was noticeably "soft".

The water-free treatment mixture was applied to the matrix in the same manner as described in Example I.

Individual towels made from the water-free treated matrix were applied to skin by contact. This contact transferred a thin film of the mixture to the skin. The skin felt noticeably lubricious. These same towels, when contacted with wet skin, created an unstable emulsion that also transferred the lubricant to the skin.

| CHEMICAL COMPONENT | TRADE NAME | AMOUNT |
| --- | --- | --- |
| Propylene Glycol USP | | 39.50 |
| Polyethylene Glycol | PEG 600 | 13.15 |
| Plurafac-Alcohol Alkoxylate | D-25 | 7.71 |
| Plurafac-Alcohol Alkoxylate | B-25-5 | 7.71 |
| Alcohol Ethoxylate | Genopal 26L60 | 12.60 |
| Mineral Oil | | 9.13 |
| Benzalkonium Chloride | BTC-6 | 10.00 |
| Fragrance | | 0.20 |
| | | 100.00 |

EXAMPLE III

Medicament

A matrix consisting of 100% synthetic fiber thermally bonded to itself and weighing approximately 20–28 grams per square yard was treated with the water-free formulation listed below.

A matrix treated with only 1 time its weight of formulation was also evaluated by placing the water-free treated matrix in water and transferring the medicament from the matrix into the water.

The treatment preparation was applied as described in Example I and weighed up to four times the basis weight of the matrix.

An individual towel made using the water-free matrix was applied to the skin by contact which transferred a thin film of the mixture to the skin. Those same towels, when applied to wet skin with pressure, created an unstable emulsion which aided the transfer of the medicament to the skin under those conditions.

| CHEMICAL COMPONENT | TRADE NAME | AMOUNT |
| --- | --- | --- |
| Propylene Glycol USP | | 50.00 |
| Miconazole Nitrate | | 45.00 |
| Benzalkonium Chloride | BTC 65 | 5.00 |
| | | 100.00 |

EXAMPLE IV

By using an oil based insect repellent such as citronellol in the treatment mixture, a water-free treated matrix can be prepared which transfers the insect repellent to the skin on contact. In the presence of perspiration or water accompanied by pressure, the towels of this example form an unstable emulsion that evenly transfers the insect repellent to the skin.

EXAMPLE V

An air laid cellulose pulp and acrylic binders matrix weighing 60 grams per square yard was treated with a substantially water-free mixture of surfactants, emollients, skin protectants, preservative, fragrance and propylene glycol as listed below:

| Chemical | Function | wt. % |
|---|---|---|
| Coconut oil | Emollient | 43.32 |
| Polysorbate | Surfactant | 10.33 |
| Poly oxyproplylene stearyl ether | Surfactant | 10.33 |
| Propylene glycol | Emollient | 7.22 |
| Dimethicone | Skin Protectant | 27.00 |
| Isothiazoline | Preservative | 0.80 |
| Floragreen | Fragrance | 1.00 |
| | | 100.00 |

The substantially water-free mixture was applied to the matrix with a gravure pattern roll so that the add on to the air laid pulp matrix was 18%. The water-free treated matrix was dry to the touch and did not feel greasy. The water-free treated matrix was analyzed for weight percent Dimethicone and found to contain 4.1% which corresponds with the theoretical amount predicted on the matrix. The water-free treated matrix was carefully placed in water so that it absorbed three times its dry weight in water. When carefully squeezed only water was expressed from the wetted wipe demonstrating that no emulsion had formed.

Another similarly treated wipe was rubbed together for 10 seconds and then squeezed. An unstable emulsion was expressed from the wipe which separated into phase layers within a few seconds. The expressed liquid was analyzed for Dimethicone and 1.2% was found. This experiment demonstrated that the Dimethicone oil was temporarily emulsified into the aqueous phase and was transferable from the matrix via the dispersion medium.

EXAMPLE VI

A sonically bonded matrix of 2.2 oz/sq. yd consisting of a top and bottom layer of 0.50 oz/sq. yd spun bonded polypropylene and three inner layers of tissue was treated with the following non-aqueous formulation.

| Compound | Function | Wt. % (paper/cellulose) |
|---|---|---|
| Propylene glycol | Emollient | 25.0 |
| Polyethylene glycol 600 | Emollient | 10.0 |
| Mineral oil | Lubricant | 25.0 |
| Ethoxylated fatty alcohol | Surfactant | 30.0 |
| Quaternary fatty amine | Preservative | 10.0 |
| | | 100.0 |

The substantially water-free mixture was applied to the matrix with a gravure pattern roll so that the add on to the sonically bonded matrix was 22%. The water-free treated matrix felt dry to the touch and when rubbed on skin, no oily feel could be detected, but the skin surface repelled water. A 10 inch square of water-free treated matrix was wetted with four times its weight in water. When gently squeezed, only water was expressed from the wipe.

Another treated wipe was wetted with substantially the same weight of water and rubbed for several seconds on the surface of a forearm. An oily residue was left on the forearm demonstrating that under the influence of pressure from rubbing the treated wipe on skin in the presence of water, an unstable emulsion formed.

Therefore, I claim:

1. A dry matrix comprising:
   a. a plurality of fibers; and
   b. a film on at least part of said fibers, said film consisting essentially of a water free mixture of:
      i. at least one member selected from the group consisting of lipid emollients, lubricants and protectants; and
      ii. a surfactant.

2. The dry matrix of claim 1, wherein said surfactant comprises a glycol.

3. The dry matrix of claim 1, wherein said surfactant is a member of the group consisting of cationic and anionic surfactants.

4. The dry matrix of claim 1, wherein said plurality of fibers have regions with a hydrophobic character and regions with a hydrophilic character.

5. The dry matrix of claim 1, wherein said surfactant comprises between about 15%–50%, by weight, of said film.

6. The dry matrix of claim 1, wherein said film composition has a viscosity, at 25° C., of less than about 300 cps.

7. The dry matrix of claim 1, wherein said surfactant has a hydrophilic-lipophilic balance between about 4 and 11.

8. The dry matrix of claim 1, wherein the only water present in the said dry matrix is bound to said plurality of fibers.

9. The dry matrix of claim 1 wherein said matrix comprises substantially no added water.

10. The dry matrix of claim 2 wherein said glycol is present in an amount between about 1% and about 99% by weight of said film composition.

11. The dry matrix of claim 2 wherein said glycol is selected from the group consisting of propylene glycol, polyethylene glycol and methoxy polyethylene glycol.

12. The dry matrix of claim 2 wherein said glycol is present in an amount between about 4% and about 50% by weight of said film composition.

13. The dry matrix of claim 1, wherein said emollient is selected from the group consisting of stearyl ether, caproic esters and lanolin.

14. The dry matrix of claim 13, wherein said emollient is present in said film composition in an amount of up to about 50% by weight of said film composition.

15. The dry matrix of claim 1, wherein said lubricant is a member selected from the group consisting of mineral oil, petrolatum and wax.

16. The dry matrix of claim 15, wherein said lubricant is present in said film composition in an amount up to about 50% by weight of said film composition.

17. The dry matrix of claim 1, wherein said protectant is selected from the group consisting of dimethyl polysiloxane, cyclomethicone and lanolin.

18. The dry matrix of claim 17, wherein said protectant is present in the non-aqueous mixture in an amount up to about 50% by weight of the non-aqueous mixture.

19. The dry matrix of claim 1 additionally containing a medicament.

20. The dry matrix of claim 1, wherein said medicament is a member selected from the group consisting of zinc oxide, aloe, titanium dioxide, miconazole, bacitracin, neomycin, polymyxin, vitamins A, D, and E, salicylic acid, retinoic acid, resorcinol, benadryl, sulfadiazine, sulfaguanidine, citronellol and hydrocortisone, and is present in an amount up to about 50% by weight.

21. A method of treating a skin surface comprising:
a. Obtaining a dry matrix sheet comprising:
  i. a plurality of fibers; and
  ii. a film on at least part of said fibers, said film consisting essentially of a water free mixture of
    a) at least one member selected from the group consisting of lipid emollients, lubricants and protectants; and
    b) a surfactant; and
b. rubbing said skin surface with the said sheet.

22. The method of claim 21 wherein said film additionally contains a medicament.

23. The method of claim 22 wherein said medicament is a member selected from the group consisting of zinc oxide, aloe, titanium dioxide, miconazole, bacitracin, neomycin, polymyxin, vitamins A, D and E, salicylic acid, retinoic acid, resorcinol, benadryl, sulfadiazine, sulfaguanidine, citronellol and hydrocortisone, and is present in an amount up to about 50% by weight.

* * * * *